(12) United States Patent
Erler et al.

(10) Patent No.: US 8,324,408 B2
(45) Date of Patent: Dec. 4, 2012

(54) METHOD FOR THE PREPARATION OF DRONABINOL

(75) Inventors: Joachim Erler, Erlangen (DE); Stefan Heitner, Fuerth (DE)

(73) Assignee: Bionorica AG

( * ) Notice: Subject to any disclaimer, the term of this patent is extended or adjusted under 35 U.S.C. 154(b) by 648 days.

(21) Appl. No.: 11/993,017

(22) PCT Filed: Jun. 1, 2006

(86) PCT No.: PCT/EP2006/005250
§ 371 (c)(1),
(2), (4) Date: Apr. 20, 2010

(87) PCT Pub. No.: WO2006/136273
PCT Pub. Date: Dec. 28, 2006

(65) Prior Publication Data
US 2010/0210860 A1 Aug. 19, 2010

(30) Foreign Application Priority Data
Jun. 22, 2005 (DE) .......................... 10 2005 028 937

(51) Int. Cl.
*C07D 311/80* (2006.01)
(52) U.S. Cl. ...................................................... 549/390
(58) Field of Classification Search ................ 549/390
See application file for complete search history.

(56) References Cited

U.S. PATENT DOCUMENTS

| 4,025,516 A | 5/1977 | Razdan et al. |
| 5,342,971 A | 8/1994 | Herlt et al. |

FOREIGN PATENT DOCUMENTS

| DE | 4100441 A1 | 7/1992 |
| DE | 69201959 T2 | 8/1995 |
| DE | 10051427 C1 | 6/2002 |
| DE | 10106024 B4 | 10/2004 |
| DE | 102005028937.1 | 1/2006 |
| WO | PCT/EP06/05250 | 10/2006 |

*Primary Examiner* — Bernard Dentz
(74) *Attorney, Agent, or Firm* — Connolly Bove Lodge & Hutz LLP

(57) ABSTRACT

The present invention relates to a method for the preparation of dronabinol ((6aR-trans)-6a,7,8,10a-tetrahydro-6,6,9-trimethyl-3-pentyl-6H-dibenzo[b,d]pyran-1-ol, $\Delta^9$-tetrahydrocannabinol ($\Delta^9$-THC)) from cannabidiol (CBD) by cyclization of cannabidiol (CBD) (2-[1R-3-methyl-6-(1-methylethenyl)-2-cyclohexene-1-yl]-5-pentyl-1,3-benzoldiol) to $\Delta^9$-THC. The method according to the present invention is characterized in that cannabidiol (CBD) (B) is present in an organic solvent and cyclized to $\Delta^9$-THC in the presence of a molecular sieve while being heated.

It was found out that, in the method of the present invention, the molecular sieve not only has the previously mentioned drying properties, but also exhibits strong catalytic properties which are important in this reaction. Normally, cyclizations carried out in the presence of a Lewis acid catalyst only are distinctly slower and the $\Delta^9$-THC yield is lower than in cyclizations carried out in the present of a molecular sieve.

18 Claims, No Drawings

METHOD FOR THE PREPARATION OF DRONABINOL

RELATED APPLICATIONS

Benefit of priority is claimed under 35 U.S.C. 119(e) to German Application No. 10 2005 028 937.1 filed on Jun. 22, 2005 and International Application No. PCT/EP06/05250 filed on Jun. 1, 2006. The disclosures of the above-referenced applications are fully incorporated by reference.

The present invention relates to a method for the preparation of dronabinol (((6aR-trans)-6a,7,8,10a-tetrahydro-6,6,9-trimethyl-3-pentyl-6H-dibenzo[b,d]pyran-1-ol, $\Delta^9$-tetrahydrocannabinol ($\Delta^9$-THC)) from cannabidiol (CBD) by cyclization of cannabidiol (CBD) (2-[1R-3-Methyl-6-(1-methylethenyl)-2-cyclohexene-1-yl]-5-pentyl-1,3-benzoldiol) to $\Delta^9$-THC according to the preamble of claim 1.

*Cannabis* (hemp) is, along with the genus *Humulus* (hop), member of the Cannabidaceae family, wherein hop, for example, does not contain cannabinoids. There are two different concepts available for the botanical and chemotaxonomic differentiation of the genus *Cannabis*. There are three kinds, *Cannabis sativa* Linnaeus, *Cannabis indica* LAM and *Cannabis ruderalis*; whereas, according to another doctrine, there exists only an aggregate species *Cannabis sativa* L. composed of the subspecies *Cannabis sativa* ssp. *sativa* and ssp. *indica*. The *Cannabis* plant is, furthermore, differentiated in a drug type and a fibre type, wherein the differentiation is made on the basis of the quantitative proportions of the main cannabinoids cannabidiol (CBD) and $\Delta^9$-tetrahydrocannabinol ($\Delta^9$-THC). Fibre hemp, the cultivation of which is permitted for fibre production, must not exceed a $\Delta^9$-THC content of 0.3%, related to the plant dry matter, while the drug type my exhibit a $\Delta^9$-THC content of approx. 5%-15%, related to the plant dry matter.

In Germany, the known hallucinogen *Cannabis* preparations marijuana and hashish, like heroine, cocaine and LSD, being non marketable narcotics, are subject to the requirements of the narcotics act.

*Cannabis sativa* L. comprises more than 420 different substances and 61 compounds thereof belong to the class of cannabinoids. They are lipophilic, non-nitrogenous, mostly phenolic compounds. The neutral cannabinoids are biogenetically derived from a monoterpene and a phenol and the acidic cannabinoids are biogenetically derived from a monoterpene and a phenolic acid and exhibit a $C_{21}$-backbone structure. In the literature, there are two different numbering systems to be found for cannabinoids. The older numbering system is based on the monoterpene skeleton, whereas the newer IUPAC-terminology, which is exclusively used in the present invention, relates to the dibenzopyrane skeleton.

Thus, the ring atom numbering used in the present application for $\Delta^9$-Tetrahydrocannabinol ($\Delta^9$-THC), for example, is as follows:

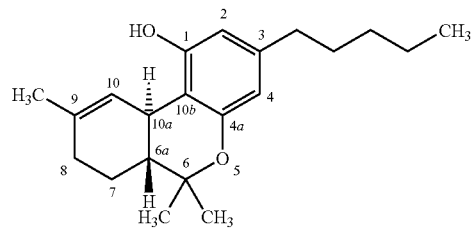

The most important cannabinoids, are, among others, as follows:

| | |
|---|---|
| $\Delta^9$-Tetrahydrocannabinol | $\Delta^9$-THC |
| $\Delta^8$-Tetrahydrocannabinol | $\Delta^8$-THC |
| Cannabichromen | CBC |
| Cannabidiol | CBD |
| Cannabigerol | CBG |
| Cannabinidiol | CBND |
| Cannabinol | CBN |

In addition to the above-mentioned cannabinoids, the respective carboxylic acids are contained in the raw drug as well as in the plant products. Normally, the carboxylic acids serve as biosynthetic precursor. This way, the tetrahydrocannabinols $\Delta^9$- and $\Delta^8$-THC are created in vivo by decarboxylation of the THC carboxylic acids, and CBD is created from the respective cannabidiol carboxylic acids.

$\Delta^8$-THC may, for example, also be created during ring formation of CBD. Under specific conditions, for example by means of acid, $\Delta^8$-THC may also be created by double bond isomerism from $\Delta^9$-THC and its carboxylic acid, respectively.

In the following, the chemical structures of some cannabinoid substances and the nomenclature of both substances of tetrahydrocannabinol, the IUPAC names of which are (6aR-trans)-6a,7,8,10a-tetrahydro-6,6,9-trimethyl-3-pentyl-6H-dibenzo[b,d]pyran-1-ol, or $\Delta^9$-THC, and (6aR-trans)-6a,7,10,10a-tetrahydro-6,6,9-trimethyl-3-pentyl-6H-dibenzo[b,d]pyran-1-ol or $\Delta^8$-THC, are shown. $\Delta^9$-THC is known under the name of dronabinol.

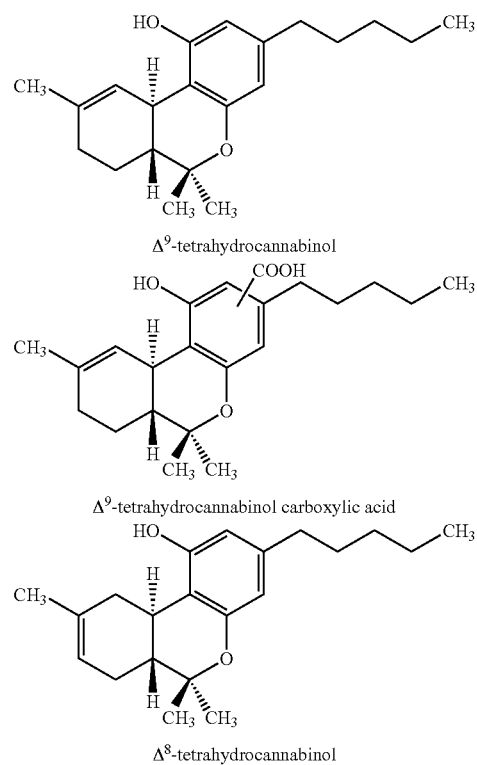

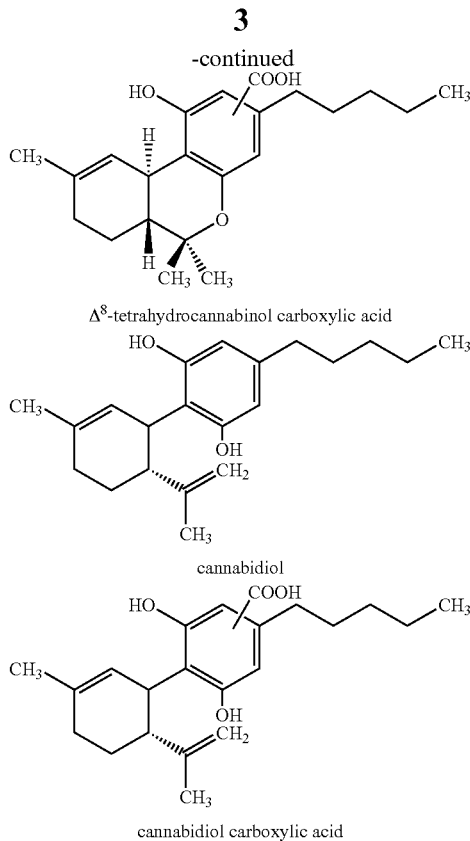

Δ⁸-tetrahydrocannabinol carboxylic acid cannabidiol cannabidiol carboxylic acid

For the purpose of the present invention, the term "tetrahydrocannabinol" or "THC" is to comprise all isomers, in particular double bond isomers, unless otherwise stated.

*Cannabis* has been a traditional drug and remedy in many cultures and for a long time. *Cannabis* was used for the treatment of various disorders—ranging from asthma to migraine—until the early 20th century. Restrictive laws on the use of *Cannabis* in the USA, however, finally led to the fact that *Cannabis* completely disappeared from the pharmacopoeias and the physicians' treatment repertoire.

These days, many of the traditional therapeutic effects are being confirmed in clinical research. Nowadays, the following indications render the pharmacological use of the substances of *Cannabis* very important:
  The appetizing effect, in particular in the case of an AIDS disease accompanied by cachexia and wasting syndrome,
  The antiemetic effect for repressing nausea and vomiting, in particular in connection with chemo therapy when cytostatic drugs are administered,
  Reduction of muscular cramps and spasticities in the context of multiple sclerosis and paraplegia,
  Pain therapy and migraine therapy—in the case of chronic pain therapy also in addition to the opioid treatment,
  Reducing the intraocular pressure with glaucoma,
  Mood-elevation,
  as well as, in particular, cannabidiol as antiepileptic.

Due to the interesting therapeutic range of cannabinoids, numerous tests were made to enrich, isolate and/or synthesize cannabinoids.

The Applicant's DE 10051427, which is herewith incorporated by reference, for example, discloses a method for the preparation of a tetrahydrocannabinol- and cannabidiol-containing extract from industrial hemp as well as *Cannabis* extracts.

DE 41 00 441 A1 describes a method for the preparation of 6,12-Dihydro-6-hydroxy-cannabidiol and its use for the production of trans-Δ⁹-tetrahydrocannabinol. DE 41 00 441 A1 in particular describes the preparation of 6,12-dihydro-6-hydroxy-cannabidiol, which is obtained by the reaction of olivetol and cis-p-menth-2-en-1,8-diol and the further reaction of same, using suitable catalysts, to trans-Δ⁹-tetrahydrocannabinol.

In the meantime, dronabinol, Δ⁹-THC, has been approved as medicament in the USA according to USP 24, p. 613 and 614. The capsular form was approved as well. According to this monographic publication, dronabinol contains no less than 95% Δ⁹-THC and not more than 2% Δ⁸-THC.

In Germany, dronabinol has been available on prescription since 1 Feb. 1998.

The cyclization of cannabidiol (CBD) (2-[1R-3-Methyl-6-(1-methylethenyl)-2-cyclohexen-1-yl]-5-pentyl-1,3-benzoldiol) to Δ⁹-THC is the important chemical step in the preparation of dronabinol ((6aR-trans)-6a,7,8,10a-tetrahydro-6,6,9-trimethyl-3-pentyl-6H-dibenzo[b,d]pyran-1-ol, Δ⁹-tetrahydrocannabinol (Δ⁹-THC)).

Various synthesis methods are known for said cyclization. First of all, there is the conventional acid-catalyzed synthesis of Petrzilka et al. (Synthese von Haschisch-Inhaltsstoffen [synthesis of hashish ingredients], *Helvetica Chimica Acta*, Vol. 52, Fasc. 4, No. 123, pp. 1102-1133 (1969)) and the method using Lewis acid as catalyst. These synthetic pathways are shown in detail in the following U.S. Pat. No. 4,025,516, R. K. Razdan, Process for the preparation of (−)₆a,10a,trans-6a,7,8,10a-tetrahydrodibenzo[b,d]-pyrans, U.S. Pat. No. 5,342,971, T. J. Herlt, Process for the Preparation of Dibenzo[b,d]-pyrans and U.S. Pat. No. 5,227,537, P. Stoss, Method for the production of 6,12-Dihydro-6-hydroxy-cannabidiol and the use thereof for the production of trans-delta-9-tetrahydrocannabinol). The use of Lewis acid catalysts is, furthermore, described in the German printed patent specification DE 101 06 024 B4 of THC Pharm GmbH, "Verfahren zur Herstellung von Dronabinol" (method for the production of dronabinol).

The disadvantage of the Δ⁹-THC-synthesis methods of the state of the art is the fact that the selectivity for Δ⁹-THC is still too low in the cyclization of CBD and a relatively huge amount of Δ⁸-THC/iso-THC is created as undesired side-product.

Based on the above described state of the art as well as on the new legal situation in the Federal Republic of Germany, it was, thus, an object of the present invention to provide a synthesis method, for the preparation of Δ⁹-THC by cyclization of CBD, with an improved selectivity for Δ⁹-THC if compared to Δ⁸-THC/iso-THC.

In terms of process-engineering, this object is solved by the characterizing features of claim 1.

Surprisingly, the inventors of the present invention found out that the use of a molecular sieve in a method for the preparation of dronabinol ((6aR-trans)-6a,7,8,10a-tetrahydro-6,6,9-trimethyl-3-pentyl-6H-dibenzo[b,d]pyran-1-ol, Δ⁹-tetrahydrocannabinol (Δ⁹-THC)) by cyclization of cannabidiol (CBD) (2-[1R-3-methyl-6-(1-methylethenyl]-2-cyclohexen-1-yl]-5-pentyl-1,3-benzoldiol) in an organic solvent had a strong impact on the selectivity regarding the Δ⁹-THC/Δ⁸-THC-ratio as well as on the reaction rate.

As described above, cyclization to Δ⁹-THC in the presence of Lewis acids is already known in the state of the art.

The inventors found out that, surprisingly, the Δ⁹-THC yield considerably increases in relation to the formed Δ⁸-THC, if the Lewis acid is replaced by a molecular sieve.

Cyclization is considerably speeded up by the use of a molecular sieve, as described in the present invention. It is possible that the molecular sieve serves as a catalyst in this process.

The usable molecular sieves are all molecular sieves known in the state of the art, in particular, however, molecular sieves basing on crystalline zeolite structures as well as molecular sieves made of synthetic zeolite analogues, such as, for example, disclosed in Kosal, M. E.; Chou, J.-H.; Wilson, S. R.; Suslick, K. S. "A Functional Zeolite Analogue Assembled From Metalloporphyrins" Nature Materials, 2002, 1, 118-121, which is, concerning this matter, herewith incorporated by reference.

Mixtures of different types of molecular sieves are usable as well.

For the use in the framework of the present invention, the molecular sieve preferably exhibits a pore size of 0.2-1 nm, preferably of 0.4 nm.

A continuous increase of the molecular sieve content in this reaction considerably accelerates reaction, this leading to a reduction of reaction time of up to 50%.

The weight ratio of $\Delta^9$-tetrahydrocannabinol cannabidiol (CBD)/molecular sieve is preferably 5:1 to 1:5, more preferably 1:1.

The use of a molecular sieve results in an increase in the $\Delta^9$-THC yield, in a considerable shift of the relation of $\Delta^9$-THC to $\Delta^8$-THC/iso-THC in favour of the $\Delta^9$-THC, in a considerable decrease of the sum of by-products, and in a reduction of by-products resulting from the degradation process of $\Delta^9$-THC because of thermal load.

Furthermore, the inventors surprisingly found that the cyclization reaction takes place, runs faster, results in better yields of $\Delta^9$-THC and a better $\Delta^9$-THC to $\Delta^8$-THC/iso-THC-ratio, compared with a catalyst reaction with a Lewis acid catalyst and in absence of a molecular sieve, if a Lewis acid catalyst is used in the presence of a molecular sieve.

Thus, in one embodiment of the present invention it is provided that a Lewis acid is additionally added to the reaction mixture. This Lewis acid may, for example, comprise zinc salts, tin(II) chlorides, magnesium salts and/or silver salts, preferably as halides or trifluoromethanesulfonates. It is particularly preferred to use zinc(II) bromide as Lewis acid.

If CBD is reacted with a molecular sieve and a Lewis acid during the cyclization reaction, the weight ratio CBD/molecular sieve/Lewis acid preferably is between 5:1:1, 1:5:1 and 1:1:5, preferably 1:2:2 or 1:2:3 and, more preferably, 1:1:3, in order to obtain an optimum $\Delta^9$-THC/$\Delta^8$-THC-ratio.

In order to obtain as high yields of $\Delta^9$-THC as possible, CBD is reacted with mixtures from Lewis acids and molecular sieve, wherein the molecular sieve proportion in the mixture is the same as, or higher than, the Lewis acid proportion.

If the molecular sieve proportion is too high, the reaction rate is further accelerated but the $\Delta^9$-THC yields decrease.

In one embodiment of the present invention, it is preferred that the cannabidiol dissolved in a solvent is contacted with the molecular sieve, optionally in the presence of a Lewis acid, with heating, preferably under reflux.

In order to further accelerate the reaction rate, it is particularly preferred to heat the reaction mixture to its boiling point.

First of all, suitable solvents are all organic solvents in which cannabidiol is soluble.

The solvent is preferably selected from the group consisting of aliphatic hydrocarbons, in particular, n-pentane, n-hexane, n-heptane; aromatic hydrocarbons, in particular benzene, toluene, xylene; halogenated hydrocarbons, in particular dichloromethane, dichloroethane, 1,1,1-trichloroethane, trichloroethene, tetrachloroethene, methylene chloride; petroleum ethers; cyclic aliphatics, in particular cyclohexane and mixtures thereof.

The inventors assume that water residues possibly contained in the organic solvents, might support the formation of a thermodynamically more stable $\Delta^8$-THC. However, the inventors do not wish to be bound to this theory.

Thus, according to one embodiment of the present invention, the solvent preferably is substantially anhydrous, more preferably pre-dried.

Furthermore, the complete reaction is preferably carried out in an inert atmosphere ($N_2$, Ar or mixtures thereof, for example).

For said pre-drying, sodium, sodium-, calcium-, magnesium sulfate and/or a molecular sieve may be used, for example.

It is furthermore preferred that the Lewis acid optionally added becomes substantially anhydrous.

Upon the successful completion of the cyclization of cannabidiol (CBD) to dronabinol ($\Delta^9$-tetrahydrocannabinol ($\Delta^9$-THC)) and the side-product $\Delta^8$-THC, the desired $\Delta^9$-THC may be purified from the mixture of $\Delta^9$-THC/$\Delta^8$-THC, for example, by means of a preparative HPLC column with modified silica gel, for example type C8 or type C18.

For this, the cyclization reaction mixture is dissolved in an organic solvent or solvent mixture.

Suitable are, among others, aliphatic hydrocarbons, in particular, pentane, hexane, n-hexane, n-heptane; aromatic hydrocarbons, in particular benzene, toluene, xylene; halogenated hydrocarbons, in particular dichloromethane, dichloroethane, 1,1,1-trichloroethene, trichloroethene, tetrachloroethene, methylene chloride; petroleum ethers; cyclic aliphatics, in particular cyclohexane and mixtures thereof.

The solvent mixture with the reaction mixture contained therein is applied to the preparative HPLC column.

In this context, the exact method for separation of the substances depends on the kind of column and solvents used. It is within the scope of the knowledge of the person skilled in the art to ideally adapt the respective separation method to the given parameters.

Upon completion of the separation, distillation is used to liberate the dronabinol ($\Delta^9$-THC) obtained from the solvent.

Thus, the present inventors surprisingly found out that the molecular sieve not only has the above-mentioned drying properties, but also has strong catalytic properties which are important in this reaction.

Normally, cyclizations based solely on the Lewis acid catalyst are definitely slower and the $\Delta^9$-THC yield is lower than in cyclizations carried out in the presence of a molecular sieve.

Further advantages and features of the present invention will become apparent from the description of embodiments.

EXAMPLE 1

0.5 g molecular sieve having a pore size of 0.4 nm (perlform, ~2 mm) is added to a solution of 0.5 g cannabidiol (CBD) in 80 ml heptane. The solution is boiled under reflux. HPLC analysis was used to determine the percentages of the components after 4 hours.

If CBD is reacted to $\Delta^9$-THC without zinc(II) bromide as Lewis acid and with a molecular sieve, approx. 28% of the educt are degraded within the first four hours of reaction. The percentages of CBD (ca. 72%), $\Delta^9$-THC (23.0%) and Δ8-THC/iso-THC (3.5%) are determined by means of HPLC analysis. The ratio of Δ9-THC to Δ8-THC/iso-THC is 6.6:1.

EXAMPLE 2

0.5 g zinc(II) bromide is added to a solution of 0.5 g cannabidiol (CBD) in 80 ml heptane. The solution is boiled under reflux. HPLC analysis was used to determine the percentages of the components after 4 hours.

If CBD is reacted to Δ9-THC with zinc(II) bromide as Lewis acid and without molecular sieve, approx. 11% of the educt are degraded within the first four hours of reaction. The percentages of CBD (approx. 89%), Δ9-THC (approx. 6.5%) and Δ8-THC/iso-THC (approx. 2.0%) are determined by means of HPLC analysis. The ratio of Δ9-THC to Δ8-THC/iso-THC is 3.2:1.

EXAMPLE 3

0.5 g zinc(II) bromide is added to a solution of 0.5 g cannabidiol (CBD) in 80 ml heptane. The amount of molecular sieve (pore size 0.4 nm) is varied from 0.5 g to 2.5 g. The solution is boiled under reflux. HPLC analysis was used to determine the percentages of the components after 4 and 7 hours.

| a) Percentages after 4 hours | | | | | | |
|---|---|---|---|---|---|---|
| Amount | Amount of | Amount of | | Parts by weight | | |
| of CBD [%] | Δ9-THC [%] | Δ8-THC [%] | Δ9-THC/ Δ8-THC | CBD | Molecular sieve | Zinc(II) bromide |
| 81.7 | 14.1 | 1.8 | 7.8 | 1 | 1 | 1 |
| 72.2 | 22.2 | 3.6 | 6.1 | 1 | 2 | 1 |
| 46.8 | 44.5 | 6.0 | 7.4 | 1 | 3 | 1 |
| 32.6 | 54.6 | 9.4 | 5.8 | 1 | 5 | 1 |

| b) Percentages after 7 hours | | | | | | |
|---|---|---|---|---|---|---|
| Amount | Amount of | Amount of | | Parts by weight | | |
| of CBD [%] | Δ9-THC [%] | Δ8-THC [%] | Δ9-THC/ Δ8-THC | CBD | Molecular sieve | Zinc(II) bromide |
| 69.5 | 25.9 | 3.0 | 8.6 | 1 | 1 | 1 |
| 56.2 | 35.4 | 5.2 | 6.8 | 1 | 2 | 1 |
| 29.9 | 60.5 | 8.5 | 7.1 | 1 | 3 | 1 |
| 15.9 | 66.8 | 12.9 | 5.2 | 1 | 5 | 1 |

EXAMPLE 4

0.5 g zinc(II) bromide is added to a solution of 1.0 g cannabidiol (CBD) in 80 ml heptane. The amount of molecular sieve (pore size 0.4 nm) is varied from 0.5 g to 2.5 g. The solution is boiled under reflux. HPLC analysis was used to determine the percentages of the components after 4 and 7 hours.

| a) Percentages after 4 hours | | | | | | |
|---|---|---|---|---|---|---|
| Amount | Amount of | Amount of | | Parts by weight | | |
| of CBD [%] | Δ9-THC [%] | Δ8-THC [%] | Δ9-THC/ Δ8-THC | CBD | Molecular sieve | Zinc(II) bromide |
| 81.7 | 14.9 | 2.1 | 7.1 | 1 | 1 | 2 |
| 55.0 | 38.4 | 4.2 | 9.1 | 1 | 2 | 2 |
| 51.3 | 40.3 | 5.5 | 7.3 | 1 | 3 | 2 |
| 27.4 | 60.2 | 9.8 | 6.1 | 1 | 5 | 2 |

| b) Percentages after 7 hours | | | | | | |
|---|---|---|---|---|---|---|
| Amount | Amount of | Amount of | | Parts by weight | | |
| of CBD [%] | Δ9-THC [%] | Δ8-THC [%] | Δ9-THC/ Δ8-THC | CBD | Molecular sieve | Zinc(II) bromide |
| 66.7 | 28.6 | 3.1 | 9.2 | 1 | 1 | 2 |
| 26.4 | 64.4 | 6.7 | 9.6 | 1 | 2 | 2 |
| 25.2 | 63.3 | 9.1 | 6.9 | 1 | 3 | 2 |
| 5.8 | 75.8 | 15.1 | 5.0 | 1 | 5 | 2 |

EXAMPLE 5

0.5 g zinc(II) bromide is added to a solution of 1.5 g cannabidiol (CBD) in 80 ml heptane. The amount of molecular sieve (pore size 0.4 nm) is varied from 0.5 g to 2.5 g. The solution is boiled under reflux. HPLC analysis was used to determine the percentages of the components after 4 and 7 hours.

| a) Percentages after 4 hours | | | | | | |
|---|---|---|---|---|---|---|
| Amount | Amount of | Amount of | | Parts by weight | | |
| of CBD [%] | Δ9-THC [%] | Δ8-THC [%] | Δ9-THC/ Δ8-THC | CBD | Molecular sieve | Zinc(II) bromide |
| 82.8 | 13.7 | 1.8 | 7.4 | 1 | 1 | 3 |
| 59.0 | 35.2 | 4.0 | 8.8 | 1 | 2 | 3 |
| 41.7 | 49.0 | 6.2 | 7.9 | 1 | 3 | 3 |
| 28.2 | 59.1 | 10.1 | 5.8 | 1 | 5 | 3 |

| b) Percentages after 7 hours | | | | | | |
|---|---|---|---|---|---|---|
| Amount | Amount of | Amount of | | Parts by weight | | |
| of CBD [%] | Δ9-THC [%] | Δ8-THC [%] | Δ9-THC/ Δ8-THC | CBD | Molecular sieve | Zinc(II) bromide |
| 69.5 | 26.5 | 2.7 | 9.8 | 1 | 1 | 3 |
| 32.0 | 59.6 | 6.9 | 9.7 | 1 | 2 | 3 |
| 14.0 | 73.0 | 9.1 | 7.7 | 1 | 3 | 3 |
| 10.3 | 72.2 | 14.4 | 5.0 | 1 | 5 | 3 |

The invention claimed is:
1. A method for the preparation of dronabinol (A) ((6aR-trans)-6a,7,8,10a-tetrahydro-6,6,9-trimethyl-3-Pentyl-6H-dibenzo[b,d]pyran-1-ol, Δ9-tetrahydrocannabinol (Δ9-THC)) from cannabidiol (CBD) (B) ((2-[1R-3-methyl-6-(1-methyl-ethenyl)-2-cyclohexen-1-yl]-5-pentyl-1,3-benzoldiol))

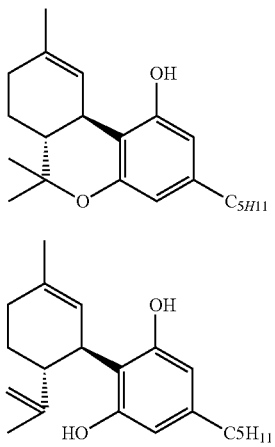

comprising the steps of:
(a) providing cannabidiol (CBD)(B) in an organic solvent; and
(b) cyclizing the CBD to $\Delta^9$-THC in the presence of a molecular Sieve, as catalyst with heating.

2. The method according to claim 1 wherein the cannabidiol dissolved in a solvent is contacted with the molecular sieve while being boiled under reflux.

3. The method according to claim 1 wherein the cannabidiol-solvent mixture is heated until the boiling point of the reaction mixture comprising molecular sieve and cannabidiol according to claim 1 is reached.

4. The method according to claim 1 wherein the solvent is substantially anhydrous.

5. The method according to claim 1 wherein the solvent is selected from the group consisting of aliphatic hydrocarbons, aromatic hydrocarbons, halogenated hydrocarbons, cyclic aliphatics, and mixtures thereof.

6. The method according to claim 5 wherein the solvent is an aliphatic hydrocarbon and the aliphatic hydrocarbon is selected from the group consisting of pentane, hexane, n-hexane, n-heptane, and mixtures thereof.

7. The method according to claim 5 wherein the solvent is an aromatic hydrocarbon and the aromatic hydrocarbon is selected from the group consisting of benzene, toluene, xylene, and mixtures thereof.

8. The method according to claim 5 wherein the solvent is a halogenated hydrocarbon and the halogenated hydrocarbon is selected from, the group consisting of dichloromethane, dichloroethane, 1,1,1-triohlotoethane, trichloroethene, tetrachloroethene, methylene chloride; petroleum ethers, and mixtures thereof.

9. The method according to claim 5 wherein the solvent is a cyclic aliphatic and the cyclic aliphatic is cyclohexane.

10. The method according to claim 1 wherein the solvent is pre-dried.

11. The method according to claim 10, wherein the pre-drying is carried out using sodium, sodium sulfate, calcium sulfate, magnesium sulfate and/or a molecular sieve.

12. The method according to claim 1 wherein the cyclization is carried out in an inert atmosphere.

13. The method according to claim 12 wherein the inert atmosphere comprises $N_2$, Ar or mixtures thereof.

14. The method according to claim 1 wherein the molecular sieve has a pore size of 0.2-1 nm.

15. The method according to claim 14 wherein the molecular sieve has a pore size of 0.4 nm.

16. The method according to claim 1 wherein the weight ratio of cannabidiol (B)/molecular sieve is 5:1 to 1:5.

17. The method according to claim 16 wherein the weight ratio of cannabidiol (B)/molecular sieve is 1:1.

18. The method, according to claim 1 wherein the molecular sieve is selected from molecular sieves on the basis of crystalline zeolite structures or molecular sieves on the basis of synthetic zeolite analogues.

* * * * *